United States Patent [19]
Petrich et al.

[11] Patent Number: 6,095,814
[45] Date of Patent: Aug. 1, 2000

[54] DISPENSING CARTRIDGE WITH STEPPED CHAMBER

[75] Inventors: Robert W. Petrich, Woodbury; Thomas W. Martin, Little Canada; James R. Kvitrud, White Bear Lake, all of Minn.

[73] Assignee: 3M Innovative Properties Company, St. Paul, Minn.

[21] Appl. No.: 09/240,389

[22] Filed: Jan. 29, 1999

[51] Int. Cl.[7] .................................................. A61C 5/04
[52] U.S. Cl. .............................. 433/90; 604/232; 604/2; 222/137
[58] Field of Search ............... 433/90, 89; 222/325, 222/326, 327, 386; 604/57, 59, 232, 233, 235, 2

[56] References Cited

U.S. PATENT DOCUMENTS

| | | | |
|---|---|---|---|
| 3,023,751 | 3/1962 | Lipsky et al. | 604/235 |
| 3,581,399 | 6/1971 | Dragan | 32/60 |
| 3,823,715 | 7/1974 | Holanek et al. | 604/59 |
| 3,827,147 | 8/1974 | Condon | 433/90 |
| 4,138,816 | 2/1979 | Warden et al. | 433/90 |
| 4,198,756 | 4/1980 | Dragan | 222/326 |
| 4,391,590 | 7/1983 | Dougherty | 433/90 |
| 4,472,141 | 9/1984 | Dragan | 433/90 |
| 4,790,819 | 12/1988 | Li et al. | 604/59 |
| 4,892,481 | 1/1990 | Kopunek et al. | 433/90 |
| 5,083,921 | 1/1992 | Dragan | 433/90 |
| 5,100,320 | 3/1992 | Martin et al. | 433/90 |
| 5,129,825 | 7/1992 | Discko, Jr. | 433/90 |
| 5,195,663 | 3/1993 | Martin et al. | 222/327 |
| 5,267,859 | 12/1993 | Discko, Jr. | 433/90 |
| 5,286,257 | 2/1994 | Fischer | 604/82 |
| 5,297,698 | 3/1994 | Martin | 222/95 |
| 5,306,147 | 4/1994 | Dragan et al. | 433/90 |
| 5,336,088 | 8/1994 | Discko, Jr. | 433/90 |
| 5,445,523 | 8/1995 | Fischer et al. | 433/90 |
| 5,460,523 | 10/1995 | Schulman | 433/90 |
| 5,620,423 | 4/1997 | Eykmann et al. | 604/217 |
| 5,647,856 | 7/1997 | Eykmann et al. | 604/181 |
| 5,697,918 | 12/1997 | Fischer et al. | 604/227 |
| 5,743,436 | 4/1998 | Wilcox | 222/137 |

FOREIGN PATENT DOCUMENTS

| | | |
|---|---|---|
| 0806187 | of 0000 | European Pat. Off. |
| 08243160 | of 0000 | Japan . |

*Primary Examiner*—Gene Mancene
*Assistant Examiner*—Pedro Philogene
*Attorney, Agent, or Firm*—James D. Christoff

[57] ABSTRACT

A dispensing cartridge for use with a hand-held applicator has a chamber with a first section and a second section. The second section has a smaller cross-sectional area than the first section such that the chamber has a stepped configuration. A piston is slidably received in the chamber and has a head portion that is received in the second section and a tail portion that is received in the first section. As a force is applied to the tail portion, the head portion advances to expel material through an outlet opening. The cartridge is especially useful for dispensing compositions having a relatively high viscosity such as dental pastes and the like.

24 Claims, 2 Drawing Sheets

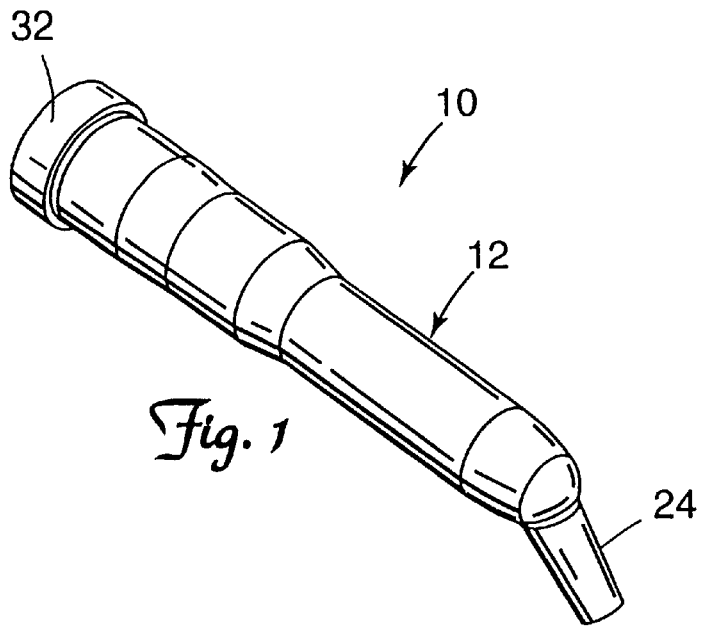
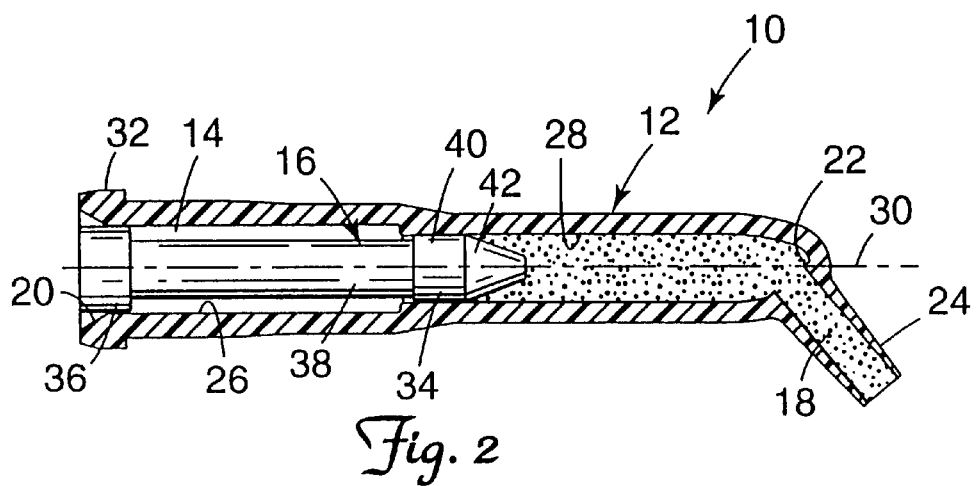
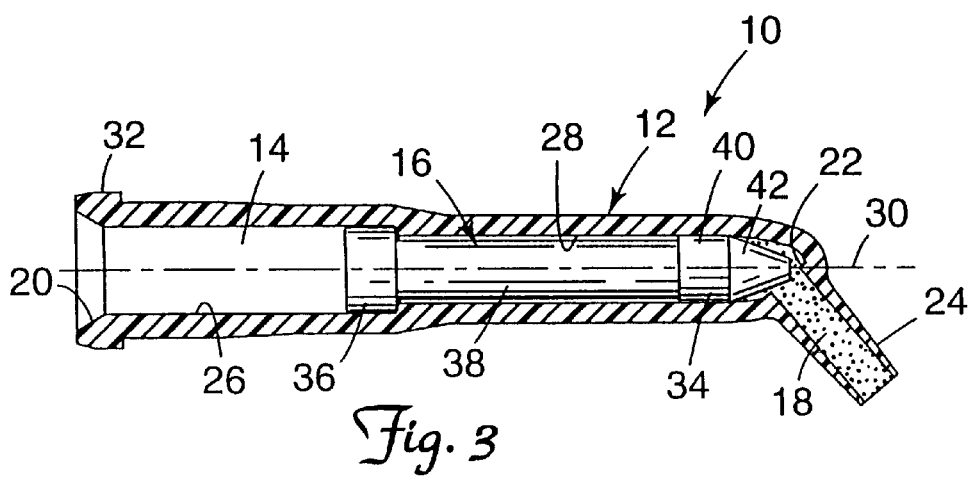

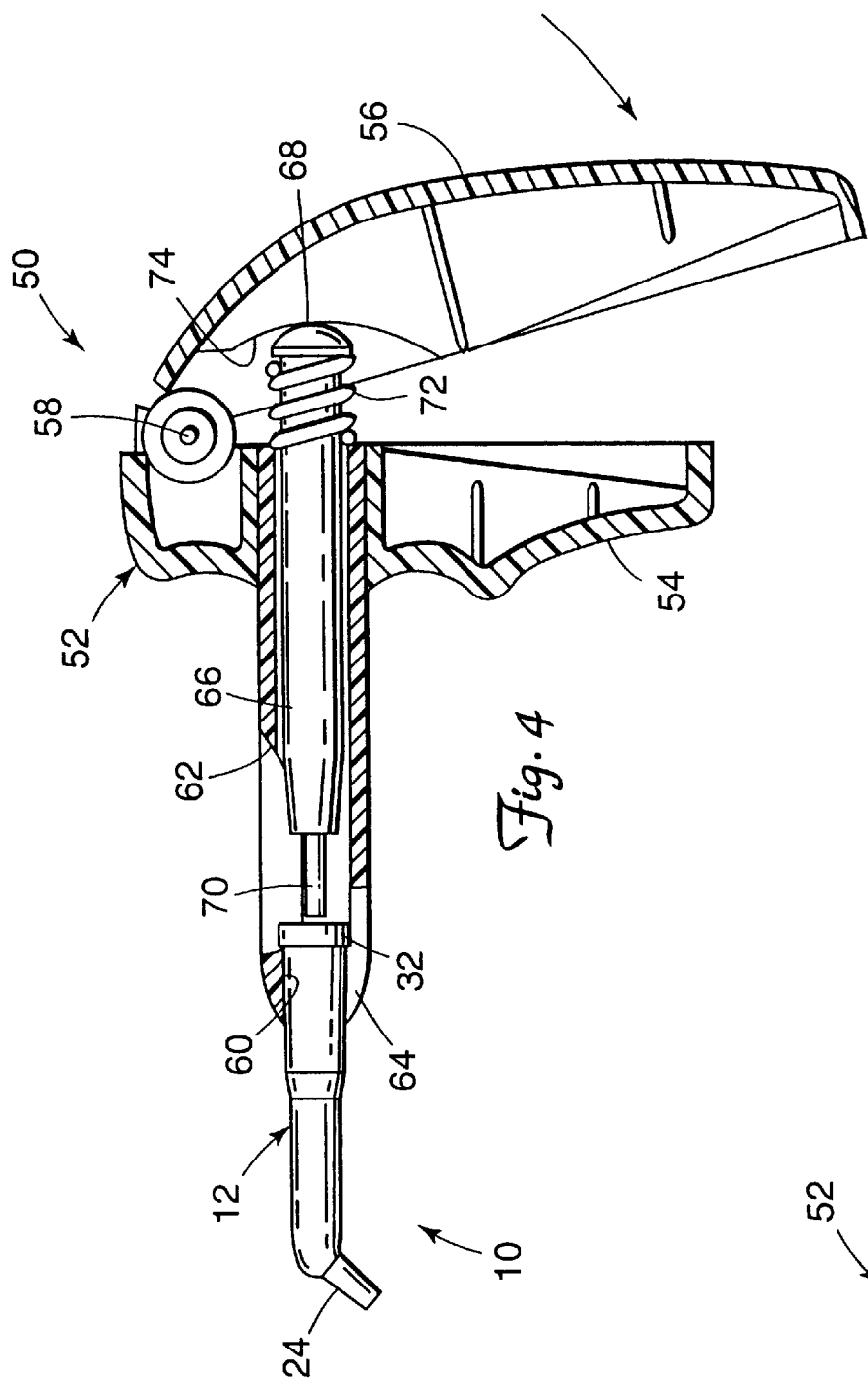
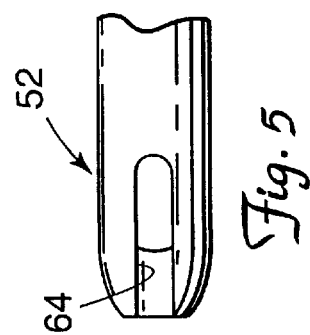

DISPENSING CARTRIDGE WITH STEPPED CHAMBER

BACKGROUND OF THE INVENTION

1. Field of the Invention

The present invention relates to a disposable dispensing cartridge of the type adapted to be releasably received in a hand-held applicator having a movable plunger.

2. Description of the Related Art

A number of hand-held dispensing devices are available for dispensing various types of materials. In many instances, the dispensing device is an assembly that includes a reusable dispenser or applicator and a disposable cartridge. The cartridge contains a quantity of a composition or material to be dispensed and is releasably received in a receptacle of the applicator.

In some dispensing assemblies that include an applicator and a cartridge, the applicator has a plunger that is advanced by the user during a dispensing operation. Often, the plunger is received in an open end of the cartridge and bears against a piston within the cartridge. As the plunger is advanced to move the piston, the piston expels a quantity of material through a front outlet opening of the cartridge.

Dispensing devices that include a reusable applicator and a disposable cartridge are favored in many instances, especially in instances where the applicator is relatively expensive in comparison to the cost of the cartridge. For example, many applicators have a movable lever or arm for facilitating advancement of the plunger. Some applicators have a ratchet mechanism associated with the arm or lever for enhancing control over movement of the plunger. Obviously, it is desirable to reuse such applicators in order to reduce costs and avoid disposal issues.

Dispensing devices with disposable cartridges are often used in the field of dentistry for dispensing dental compositions such as restoratives, adhesives, cements, etching gels, sealants and the like. In some instances, the cartridge and the front portion of the applicator receiving the cartridge are relatively small so that the cartridge can be readily maneuvered in the oral cavity during a dispensing operation. In that manner, the dental material contained in the cartridge may be conveniently dispensed directly onto the tooth structure as needed.

Examples of hand-held applicators (also called dispenser or ejector-type guns) that have been used in dentistry are described in U.S. Pat. Nos. 4,198,756, 4,391,590 and 4,472,141. Examples of cartridges (also known as capsules) useful with those applicators are described, for example, in U.S. Pat. Nos. 4,391,590, 4,767,326, 5,100,320 and 5,624,260.

In the field of dentistry, dispensing cartridges are often relatively small and adapted to be used with a single patient. The cartridge is disposed of after the procedure has been accomplished and the applicator is disinfected before use with a subsequent patient. In this manner, the risk of transferring an infectious disease from one patient to another is substantially reduced.

However, many of the dental applicators and disposable cartridges that are presently commercially available are not satisfactory for use in dispensing paste-like compositions having a relatively high viscosity. In such instances, the user must apply a relatively high force to the lever of the applicator in order to eject the composition from the cartridge. As can be appreciated, precise control over placement of the discharged composition in the oral cavity can be hindered whenever the user must exert an undue effort to expel the composition from the cartridge.

As a result, dental practitioners in the past have often used a spatula or other similar tool for placing high viscosity paste-like compositions (such as restorative materials) in the oral cavity. This practice involves placing a small quantity of the material onto the spatula and then maneuvering the spatula as needed to place and transfer the material onto the patient's tooth structure. As can be appreciated, such practice is somewhat time consuming and not as convenient as dispensing methods that involve dispensing dental compositions from a cartridge directly onto the tooth structure.

In some instances, syringes having a plunger that is advanced by a thumb screw have been used to dispense viscous dental compositions. The thumb screw provides a substantial mechanical advantage so that relatively viscous compositions can be dispensed without undue effort. However, such dispensing typically involves the use of both hands of the practitioner, one hand being used to hold the body of the syringe while the other hand is used to turn the thumb screw. Moreover, such devices are generally not used to dispense a composition directly to a patient's tooth structure.

As such, there is a need in the art for a cartridge especially adapted for use for one-handed dispensing of high viscosity compositions. Preferably, such a cartridge could be used with commercially available applicators so that a specially-made applicator is unnecessary. Moreover, there is a need in the art to provide a dispensing cartridge for use with high viscosity compositions that is especially suitable for use by dental practitioners in order to dispense a precise quantity of such compositions directly onto a tooth surface and at an exact location as desired without undue effort.

SUMMARY OF THE INVENTION

The present invention is directed in one aspect toward a dispensing cartridge for use with a hand-held applicator. The cartridge comprises a body having an open end for receiving a plunger of an applicator. The body also includes an outlet opening and an elongated chamber extending between the open end and the outlet opening. The chamber has a first section adjacent the open end and a second section adjacent the outlet opening. The first section has a certain generally constant cross-sectional area transverse to the longitudinal axis of the chamber as the outlet opening is approached. The second section has a certain generally constant cross-sectional area transverse to the longitudinal axis of the chamber as the outlet opening is approached that is less than the certain generally constant cross-sectional area of the first section. The cartridge also includes an elongated piston slidably received in the chamber. The piston has a head portion and a tail portion. The tail portion is received in the first section and the head portion is received in the second section.

In another aspect, the present invention is also directed to a dispensing cartridge for use with a hand-held applicator. In this aspect, the cartridge includes a body having an open end for receiving a plunger of the applicator. The body also includes an outlet and an elongated chamber extending between the open end and the outlet. The chamber has a first generally cylindrical section with a certain diameter and a second generally cylindrical section with a diameter that is less than the diameter of the first section. The cartridge also includes an elongated piston slidably received in the chamber. The piston has a head portion received in the second section of the chamber and a tail portion received in the first section of the chamber. The head portion includes a segment having a diameter that is approximately the same as the diameter of the second section of the body. The cartridge also includes a quantity of composition received in the chamber between the head portion of the piston and the outlet. The head portion directs the composition toward the outlet as the piston is moved by the plunger in a direction away from the open end.

Another aspect of the present invention relates to a method of dispensing a dental composition. The method includes the act of providing a cartridge having a chamber with a first generally cylindrical section and a second generally cylindrical section, wherein the second section has a diameter that is less than the diameter of the first section. The method also includes the act of advancing a piston in the chamber by bearing against a tail portion of the piston located in the first chamber section, such that a head portion of the piston located in the second chamber section urges a dental composition in the second chamber section through an outlet opening.

The invention in its various aspects as described above is a significant advantage, in that less force is needed to dispense the composition from the second section of the chamber. As a result, the invention is particularly useful for dispensing paste-like materials having a relatively high viscosity such as highly filled dental restorative compositions. Such materials can be readily dispensed by one hand of the user without undue effort, so that the dispensing operation is facilitated and the material can be dispensed in a precise location as intended.

The present invention provides a number of additional benefits that are described below in the paragraphs that follow. Other aspects and features of the invention are also set out in the detailed description and illustrated in the accompanying drawings.

BRIEF DESCRIPTION OF THE DRAWINGS

FIG. 1 is a perspective view of a dispensing cartridge constructed according to one embodiment of the invention;

FIG. 2 is an enlarged side cross-sectional view of the dispensing cartridge shown in FIG. 1, illustrating an outer body of the cartridge as well as an internal piston of the cartridge;

FIG. 3 is a view somewhat similar to FIG. 2 except that the piston has been advanced in order to expel a composition from the cartridge;

FIG. 4 is a reduced side cross-sectional view of a hand-held applicator along with the dispensing cartridge of FIGS. 1–3, wherein the dispensing cartridge is received in a receptacle of the applicator for use in a dispensing operation; and FIG. 5 is an enlarged, fragmentary bottom view of a front portion of the applicator alone that is shown in FIG. 4.

DETAILED DESCRIPTION OF THE PREFERRED EMBODIMENTS

An example of a dispensing cartridge constructed in accordance with the principles of the present invention is illustrated in FIGS. 1–4 and is broadly designated by the numeral 10. The cartridge 10 includes a body 12 having a chamber 14. The cartridge 10 also includes a piston 16 that is movable in the chamber 14 to dispense a composition 18 from the chamber when desired.

In more detail, the body 12 includes an open inlet end 20 and an outlet or outlet opening 22 that is remote from the open end 20. The outlet opening 22 is part of a passage that extends through a discharge nozzle 24 that is integrally connected to the body 12. The chamber 14 is elongated and extends from the open end 20 to a location adjacent the outlet opening 22.

The chamber 14 includes a first, rear cylindrical section 26 and a second, front cylindrical section 28. The first section 26 is adjacent the open end 20 and the second section 28 is adjacent the outlet opening 22. The central longitudinal axes of both of the sections 26, 28 are collinear with the longitudinal axis of the chamber 14. In FIGS. 2 and 3, the longitudinal axis of the chamber 14 is designated by the numeral 30.

The diameter of the second chamber section 28 is less than the diameter of the first chamber section 26. Consequently, the cross-sectional area of the second chamber section 28 is less than the cross-sectional area of the first chamber section 26 when considered in reference planes transverse to the longitudinal axis 30. As such, the chamber 14 presents a stepped configuration, with a smaller cross-sectional area as the outlet opening 22 is approached.

Preferably, the outer surface of the body 12 also presents a stepped appearance, the advantage of which will be described in the paragraphs below. As shown in the drawings, the outer diameter of the body 12 adjacent the second chamber section 28 is less than the outer diameter of the body 12 adjacent the first chamber section 26. Optionally, a tapered transition wall having the shape of a truncated cone extends between the major extent of the outer wall surrounding the first chamber section 26 and the major extent of the outer wall surrounding the second chamber section 28.

The cartridge body 12 also preferably includes a rear flange 32 that circumscribes the open end 20. The rear flange 32 is useful for retaining the cartridge 10 in an applicator as described below. Optionally, a rear external wall of the rear flange 32 is chamfered as can be appreciated, for example, by reference to FIGS. 2 and 3, although, as an alternative the flange 32 could have a 90 degree rear outer corner if desired.

As another option, the open end 20 includes a chamfered portion that leads to the chamber 14. The chamfer near the open end 20 facilitates insertion of the piston 16 during assembly of the cartridge 10. Additionally, a small chamfer is optionally provided in the chamber 14 between the sections 26, 28 in order to help reduce stress concentrations in the body 12.

The piston 16 is elongated and includes a head portion 34 and a tail portion 36. The piston 16 also includes an elongated shank 38 that integrally interconnects the head portion 34 and the tail portion 36.

The head portion 34 of the piston 16 includes a cylindrical segment 40 and a tapered, preferably frustoconical segment 42 that is integrally connected to the cylindrical segment 40. The frustoconical segment 42 has a flat front end. The cylindrical segment 40 has an outer diameter that is approximately the same as the inner diameter of the second chamber section 28. Preferably, the segment 40 is integral with remaining portions of the piston 16, although other constructions are also possible. For example, in an alternative construction the segment 40 is an initially separate seal or O-ring that is connected to a piston head.

The tail portion 36 of the piston 16 also has a cylindrical shape, and preferably has an outer diameter that is approximately the same as or slightly smaller than the diameter of the first chamber section 26. Preferably, the shank 38 has a cross-sectional area in sections transverse to the longitudinal axis of the piston 16 that is less than the cross-sectional area of the head portion 34 and the tail portion 36 in sections transverse to the longitudinal axis of the piston 16. The reduced cross-sectional area of the shank 38 helps to decrease frictional resistance to advancement of the piston 16. Optionally, the shank 38 also has a cylindrical configuration with a central axis that is collinear with the central axes of the cylindrical segment 40 and the tail portion 36.

Suitable materials for the piston 16 include plastics such as polypropylene. An example of a suitable polypropylene material is No. 3467 from Fina.

Suitable materials for the body 12 also include plastic materials. An example of a suitable plastic material for the body 12 is a nylon resin such as Zytel brand nylon resin, No. 101L from DuPont. Other examples of suitable materials for the cartridge body 12 are described in U.S. Pat. Nos. 5,624,260 and 5,100,320, both of which are incorporated by reference herein.

Preferably, the cylindrical segment 40 of the piston head portion 34 has an outer diameter that is sufficiently large to present a seal between the piston head portion 34 and the inner wall portions of the body 12 surrounding the second section 28, so that the composition 18 is effectively discharged through the outlet opening 22 as the piston 16 is advanced. Preferably, the cylindrical segment 40 presents a slight interference fit with the chamber wall portions surrounding the second chamber section 28 to provide an effective seal. As an example, when the cartridge body 12 is made of the nylon resin described above and the piston 16 is integrally made of a polypropylene material as described above, the cylindrical segment 40 may have an outer diameter of 0.132 in. (3.35 mm) while the inner wall portions of the body 12 surrounding the second chamber section 28 may have an internal diameter of 0.130 in. (3.3 mm).

Preferably, the diameter of the tail portion 36 is sufficient to retain the longitudinal axis of the piston 16 in substantial alignment with the longitudinal axis 30 of the chamber 14. However, it is preferred that the outer diameter of the tail portion 36 is not unduly large so that it does not present significant frictional resistance to advancement of the piston 16 in the chamber 14. As an example, the tail portion 36 may have an outer diameter of 0.166 in. (4.2 mm) while the first chamber section 26 has a diameter of 0.170 in. (4.3 mm).

In the embodiment illustrated in the drawings, the discharge nozzle 24 is integrally connected to the body 12 and has a longitudinal, central axis that extends at an acute angle relative to the longitudinal axis 30 of the chamber 14. However, other constructions are also possible. For example, the discharge nozzle 24 could extend along an axis collinear with the longitudinal axis 30 of the chamber 14. As another option, the discharge nozzle 24 may be bendable by hand to any one of a number of configurations adapted to best serve the dispensing operation at hand. Optionally, the discharge nozzle 24 is made of a hand-formable metal cannula that retains its shape once bent.

Preferably, and as shown in FIG. 2, the composition 18 initially fills the passage extending through the discharge nozzle 24 as well as the second chamber section 28 in regions in front of the piston head portion 34. In this manner, void space within the chamber 14 is reduced and the composition 18 is extruded from the cartridge 10 essentially simultaneously with initial advancement of the piston 16.

An example of a dispensing device useful for dispensing the composition 18 from the cartridge 10 is a hand-held applicator such as the applicator 50 shown in FIGS. 4 and 5. The applicator 50 as illustrated is identical to well-known applicators used in the dental field (such as 3M's dental applicator no. 5706SD) and includes a housing 52 with a depending handle 54. A rear lever 56 of the applicator 50 is connected to the housing 52 by a pivot 58 for swinging movement about a horizontal reference axis when the handle 54 extends in a vertical direction.

The front of the housing 52 includes a tubular projection having an internal cylindrical receptacle 60 for releasably receiving the cartridge 10. When the cartridge 10 is received in the receptacle 60, the cartridge 10 extends through a circular opening located at the front end of the housing 52. The circular opening has a diameter that is somewhat larger than the outer diameter of the body 12 in areas surrounding the first chamber section 26. However, the circular front opening of the housing 52 has a diameter that is somewhat smaller than the outer diameter of the rear flange 32 in order to retain the cartridge 10 in the receptacle 60.

The front tubular projection of the housing 52 also includes an upper opening 62 (FIG. 4) adjacent the receptacle 60 for inserting the cartridge 10 in the receptacle 60 when desired. The confined opening 62 is located laterally of the receptacle 60. The applicator 50 is sometimes known as a "breech-loading" applicator.

Preferably, the front tubular projection of the housing 52 includes a lower elongated slot 64 that is shown in FIG. 5. The slot 64 extends from the front end of the housing 52 and is adjacent the receptacle 60. The slot 64 conveniently provides additional clearance for the front of the cartridge 10 including the nozzle 24 when the cartridge 10 is inserted into or removed from the receptacle 60.

The applicator 50 includes an elongated plunger 66 with a rear, somewhat semi-spherical enlarged head 68. The plunger 66 also includes an elongated cylindrical shaft 70 that is preferably made of a relatively strong, wear-resistant material such as stainless steel. As shown in FIG. 4, a coiled compression spring 72 surrounds the plunger 66 and is located between the head 68 and a rear opening of a passageway through the tubular projection of the housing 52 that leads to the receptacle 60.

A drive means of the applicator 50 includes a pair of curved cam surfaces 74, one of which is illustrated in FIG. 4. The cam surfaces 74 are formed on an upper, inner portion of the lever 56 and are oriented for sliding engagement with the curved surface of the plunger head 68. As the lever 56 is moved in an arc about the pivot 58 in the direction of the arrow shown in FIG. 4, the head 68 rides along the cam surfaces 74 and moves the plunger 66 in a forward direction toward the cartridge 10 when the cartridge 10 is received in the receptacle 60.

The outer diameter of the shaft 70 is somewhat smaller than the diameter of the first chamber section 26 of the cartridge 10. As the lever 56 is pivoted in the direction of the arrow and the plunger 66 is advanced toward the cartridge 10, the shaft 70 enters the open end 20 of the cartridge 10 and bears against a rear face the tail portion 36 of the piston 16. Continued advancement of the lever 56 in the direction of the arrow moves the piston 16 forwardly, whereupon the head portion 34 of the piston 16 exerts a pressure on the composition 18 and directs the composition 18 through the outlet opening 22.

As a preferred option, the length of the piston shank 38 is selected so that the piston 16 reaches its limit of travel in a forward direction once the front annular wall of the tail portion 36 contacts the shoulder located in the chamber 14 between the first section 26 and the second section 28. Preferably, when the piston 16 has reached that forward limit of travel, the piston head portion 34 is very near the front end of the chamber 14 to ensure that substantial all of the composition 18 has been expelled from the second chamber section 28. As another option, however, the length of the piston shank 38 is selected so that the piston 16 reaches its forward limit of travel when the head portion 34 contacts the inner wall portions of the chamber 14 near or at the front end of the second chamber section 28.

The relatively small diameter of the second chamber section 28 facilitates dispensing of relatively high viscosity materials such as dental pastes. The relatively small diameter of the second chamber section 28 reduces the volume of the composition 18 that is expelled from the cartridge 10 per unit length of advancement of the piston 16, and as a consequence less force is needed to advance the piston 16 per unit length than would otherwise be needed with a chamber having a larger internal diameter. More particularly, if the pressure (in units of force per unit area) needed to advance the piston 16 and expel the composition 18 increases due to an increase in viscosity of the composition 18, the amount of force needed can remain the same if the cross-sectional area of the piston 16 is reduced. Moreover, the smaller internal diameter of the second chamber section 28 is closer in cross-sectional area to the passage through the outlet opening 22 and the discharge nozzle 24, with the result that there is less resistance to the flow of the composition 18 from the chamber 14.

The stepped configuration of the chamber 14 advantageously enables the cartridge 10 to be releasably connected to conventional applicators such as the applicator 50. By comparison, simply reducing the internal diameter of conventional cartridges would not be as advantageous as the present invention, since the resulting internal diameter of such a cartridge may be smaller than the outer diameter of the plunger shaft 70 of a conventional applicator, with the result that the user would be essentially required to purchase a new applicator having a plunger shaft with a smaller diameter. Since the first chamber section 26 of the cartridge 10 of the present invention is preferably sufficiently large to receive the plunger shaft 70 of conventional applicators such as applicator 50, the cartridge 10 may be used with applicators that are already available in the dental office and in the marketplace.

The stepped configuration of the cartridge body 12 is also an advantage in that insertion and removal of the cartridge 10 from the receptacle 60 is facilitated. For example, the user may opt to tilt the cartridge 10 relative to the receptacle 60 during insertion of the cartridge in order to more readily move the cartridge to a fully inserted or seated position with the rear flange 32 moved as far forwardly as possible toward the circular opening at the front end of the housing. The stepped configuration of the body 12 provides clearance for facilitating such tilting and advancing motions.

Moreover, the elongated configuration of the body 12 and the piston 16 provides enhanced placement of the dispensed composition 18 on its intended location. For example, if the cartridge 10 is used in a dental procedure, the increased length of the cartridge 10 facilitates locating the discharge nozzle 24 in restricted areas of the oral cavity such as posterior regions including areas of the patient's molar teeth. The relatively long cartridge 10 also improves the user's visibility during a dispensing operation, since the user's hands on the applicator 50 are located somewhat farther away from the discharge nozzle 24 and the intended area to receive the dispensed composition 18.

The cartridge 10 of the present invention is also an advantage in that the relatively long body 12 is easier to grasp and manipulate in comparison to conventional cartridges. The length of the cartridge 10 facilitates insertion and removal of the cartridge 10 from the applicator, particularly in instances where a breech-loading applicator such as applicator 50 is employed.

The cartridge 10 is particularly useful for dispensing high viscosity dental compositions such as restorative materials. Although the diameter of the second chamber section 28 is smaller than the first chamber section 26, the volume of the second section 28 is sufficient to contain enough composition 18 (along with the amount of composition contained in the discharge nozzle 24) to meet a dental practitioner's expectations (e.g., about 0.2 g of restorative material when the second chamber section 28 has a diameter of 0.13 in). However, other dental materials such as cements (e.g., luting cements and orthodontic cements), etching gels, glass ionomer cements, sealants and the like may alternatively be used. The cartridge 10 may also be used to dispense non-dental compositions such as adhesives or other materials for household, industrial, medical or other applications.

Moreover, the cartridge 10 may be used with applicators other than the applicator 50 shown in FIGS. 4 and 5. For example, applicators of the type having a side-loading receptacle may be employed. Examples of suitable alternative applicators are shown in U.S. Pat. Nos. 4,198,756, 4,391,590, 4,472,141 and 5,743,436.

EXAMPLE

Extrusion tests were conducted on both conventional dental cartridges and dental cartridges constructed according to the invention. In each test, the cartridge body was made of Zytel brand 101L nylon resin and the piston was made of polypropylene. In the conventional cartridge, the internal diameter of the cartridge chamber was 0.1575 in. (4 mm). In the cartridges of the present invention, the internal diameter of the second chamber section (corresponding to chamber section 28 as described above) was 0.128 in. (3.25 mm). An Instron universal test machine was utilized to determine the compressive force needed to advance the cartridge piston, using a crosshead speed of 50.8 mm/min. The tests were conducted in a room where the temperature and humidity were held constant.

Five empty cartridges of convention construction were tested to determine the force needed to advance the pistons in the absence of any composition in the chambers. The results were averaged and found to be 0.20 kg with a standard deviation of 0.08. The test was repeated with the cartridges of the present invention and the results when averaged were 3.51 kg with a standard deviation of 0.3.

Ten cartridges of conventional construction and ten cartridges of the invention received a quantity of Z100 dental restorative paste (from 3M Company). The paste was placed into the cartridges using a filling tube and then tamped by hand; subsequently, a piston was placed into each cartridge and pushed into the open end.

The force needed to advance the pistons of the ten filled conventional cartridges was determined and averaged 26.97 kg with a standard deviation of 2.2. The frictional force of 0.20 kg (i.e., the force needed to advance the piston of a similar empty cartridge) was subtracted, yielding a result of 26.77 kg. The test was repeated for the ten filled cartridges of the invention and it was determined that the force needed to advance the pistons averaged 19.34 kg with a standard deviation of 2.2. The frictional force of 3.5 was then subtracted to yield a result of 15.82 kg, a reduction in the amount of force of 40.9%.

The data shows that a substantial (i.e., 40.9%) reduction in extrusion force necessary to dispense a dental composition was provided by the present invention, though the inner diameter of the capsule chambers was decreased by only a relatively small amount (i.e., from 4 mm to 3.25 mm).

Those skilled in the art may recognize that various additions and modifications may be made to the presently preferred embodiments that are described in detail above without departing from the spirit of the invention. As a result, the invention should not be deemed limited to the specific embodiments that are set out above, but limited only by a fair scope of the claims that follow along with their equivalents.

What is claimed is:

1. A dispensing cartridge for releasable connection to a hand-held applicator comprising:
   a body having an open end for receiving a plunger of an applicator, the body also including an outlet opening and an elongated chamber extending between the open end and the outlet opening, the chamber having a first section adjacent the open end and a second section adjacent the outlet opening, wherein the first section has a certain generally constant cross-sectional area transverse to the longitudinal axis of the chamber as the outlet opening is approached, and wherein the second section has a certain generally constant cross-sectional area transverse to the longitudinal axis of the chamber as the outlet opening is approached that is less than the certain generally constant cross-sectional area of the first section; and
   an elongated piston slidably received in the chamber, the piston having a head portion and a tail portion, wherein the tail portion has a rear face for contact with the plunger of the applicator, wherein the tail portion including the rear face is received in the first section and wherein the head portion is received in the second section.

2. A dispensing cartridge according to claim 1 wherein the head portion includes a segment having a cross-sectional area in sections transverse to the longitudinal axis of the piston that is approximately the same as the certain generally constant cross-sectional area of the second section of the chamber.

3. A dispensing cartridge according to claim 1 wherein the tail portion has a cross-sectional area in sections transverse to the longitudinal axis of the piston that is approximately the same as the certain generally constant cross-sectional area of the first section of the chamber.

4. A dispensing cartridge according to claim 1 wherein the piston includes an elongated shank located between the head portion and the tail portion.

5. A dispensing cartridge according to claim 4 wherein the shank has a cross-sectional area in a section transverse to the longitudinal axis of the piston that is smaller than the cross-sectional area of the head portion in a section transverse to the longitudinal axis of the piston.

6. A dispensing cartridge according to claim 1 wherein the cartridge includes a discharge nozzle connected to the body and surrounding the outlet opening.

7. A dispensing cartridge according to claim 6 wherein the nozzle has a passage with a longitudinal axis that extends at an acute angle relative to the longitudinal axis of the body.

8. A dispensing cartridge according to claim 6 wherein the body includes a flange that circumscribes the open end for releasably retaining the cartridge in an applicator.

9. A dispensing cartridge according to claim 1 wherein the body includes a flange that circumscribes the open end for releasably retaining the cartridge in an applicator.

10. A dispensing cartridge according to claim 1 wherein the head portion of the piston has a tapered front segment.

11. A dispensing cartridge according to claim 1 and including a quantity of dental composition in the second section of the chamber between the head portion of the piston and the outlet opening.

12. A dispensing cartridge according to claim 1 wherein the body has an external stepped configuration.

13. A dispensing cartridge according to claim 1 wherein the first section and the second section each have generally cylindrical configurations.

14. A dispensing cartridge for releasable connection to a hand-held applicator comprising:
   a body having an open end for receiving a plunger of the applicator, the body also including an outlet and an elongated chamber extending between the open end and the outlet, wherein the chamber has a first generally cylindrical section with a certain diameter and a second generally cylindrical section with a diameter that is less than the diameter of the first section;
   an elongated piston slidably received in the chamber, the piston having a head portion received in the second section of the chamber and a tail portion received in the first section of the chamber, wherein the tail portion has a rear face located in the first section of the chamber for contact with the plunger of the applicator, wherein the head portion includes a segment having a diameter that is approximately the same as the diameter of the second section of the chamber; and
   a quantity of composition received in the chamber between the head portion of the piston and the outlet, wherein the head portion directs the composition toward the outlet as the piston is moved by the plunger in a direction away from the open end.

15. A dispensing cartridge according to claim 14 wherein the diameter of the segment of the head portion is sufficient to establish a seal with the body in the second section of the chamber as the piston is moved in a direction away from the open end.

16. A dispensing cartridge according to claim 14 wherein the piston includes an elongated shank integrally interconnecting the head portion and the tail portion.

17. A dispensing cartridge according to claim 16 wherein the shank has a generally cylindrical configuration with a diameter that is less than the diameter of the head portion.

18. A dispensing cartridge according to claim 14 wherein the cartridge includes a discharge nozzle connected to the body adjacent the second section of the chamber and surrounding the outlet.

19. A dispensing cartridge according to claim 18 wherein the discharge nozzle has a longitudinal axis that extends at an acute angle relative to the longitudinal axis of the chamber.

20. A dispensing cartridge according to claim 14 wherein the body includes a flange that circumscribes the open end for releasably retaining the cartridge in an applicator.

21. A dispensing cartridge according to claim 14 wherein the quantity of composition includes a dental composition.

22. A dispensing cartridge according to claim 14 wherein the body has an external stepped configuration.

23. A method of dispensing a dental composition comprising the acts of:
   providing a cartridge having a chamber with a first generally cylindrical section and a second generally cylindrical section, wherein the second section has a diameter that is less than the diameter of the first section;
   placing the cartridge in a receptacle of a hand-held applicator; and advancing a plunger of the applicator to bear directly against a tail portion of the piston located in the first chamber section and move the piston, such that a head portion of the piston located in the second chamber section urges a dental composition in the second chamber section through an outlet opening.

24. The method of claim 23 including the act of placing at least a portion of the cartridge in an oral cavity as the piston is advanced in order to dispense the dental composition directly onto oral structure.

* * * * *